United States Patent
Kim et al.

(10) Patent No.: US 10,426,769 B2
(45) Date of Patent: Oct. 1, 2019

(54) PHARMACEUTICAL COMPOSITION FOR PREVENTING AND TREATING OBESITY OR LIVER DISEASES, CONTAING TLR7 AGONIST

(71) Applicants: KNOTUS CO., LTD., Guri-si, Gyeonggi-do (KR); KNOTUS LIFE SCIENCE INC., Guri-si, Gyeonggi-do (KR)

(72) Inventors: Do Hyeong Kim, Incheon (KR); Sok Ho Kim, Iksan-si (KR); Jung Kee Kwon, Jeonju-si (KR)

(73) Assignees: KNOTUS CO., LTD., Guri-si, Gyeonggi-do (KR); KNOTUS LIFE SCIENCE INC., Jeongeup-si, Jeollabuk-do (KR)

( * ) Notice: Subject to any disclaimer, the term of this patent is extended or adjusted under 35 U.S.C. 154(b) by 0 days.

(21) Appl. No.: 15/577,016

(22) PCT Filed: May 4, 2016

(86) PCT No.: PCT/KR2016/004733
§ 371 (c)(1),
(2) Date: Nov. 27, 2017

(87) PCT Pub. No.: WO2016/195256
PCT Pub. Date: Dec. 8, 2016

(65) Prior Publication Data
US 2018/0161318 A1 Jun. 14, 2018

(30) Foreign Application Priority Data

Jun. 1, 2015 (KR) ........................ 10-2015-0077409

(51) Int. Cl.
| | |
|---|---|
| *A61K 31/4745* | (2006.01) |
| *A61K 9/20* | (2006.01) |
| *A61K 9/48* | (2006.01) |
| *A61K 31/437* | (2006.01) |
| *A23L 33/10* | (2016.01) |
| *A61P 1/16* | (2006.01) |
| *A61P 3/04* | (2006.01) |
| *A61K 9/68* | (2006.01) |
| *A61K 9/00* | (2006.01) |
| *A61K 9/02* | (2006.01) |
| *A61K 9/08* | (2006.01) |
| *A61K 9/16* | (2006.01) |

(52) U.S. Cl.
CPC .......... *A61K 31/4745* (2013.01); *A23L 33/10* (2016.08); *A61K 9/0019* (2013.01); *A61K 9/0058* (2013.01); *A61K 9/0095* (2013.01); *A61K 9/02* (2013.01); *A61K 9/08* (2013.01); *A61K 9/16* (2013.01); *A61K 9/20* (2013.01); *A61K 9/48* (2013.01); *A61K 31/437* (2013.01); *A61P 1/16* (2018.01); *A61P 3/04* (2018.01); *Y02A 50/463* (2018.01)

(58) Field of Classification Search
CPC .............. A61K 31/437; A61K 31/4745; A61K 9/0019; A61K 9/0058; A61K 9/0095; A61K 9/02; A61K 9/08; A61K 9/16; A61K 9/20; A61K 9/48; A61P 1/16; A61P 3/04; Y02A 50/463
See application file for complete search history.

(56) References Cited

U.S. PATENT DOCUMENTS

| | | | | |
|---|---|---|---|---|
| 7,576,068 | B2 * | 8/2009 | Averett .............. | A61K 31/4745 514/43 |
| 2005/0118272 | A1 * | 6/2005 | Besse ................... | A61K 9/0056 424/489 |
| 2005/0267144 | A1 * | 12/2005 | Mandrea .............. | A61K 31/137 514/292 |
| 2006/0062756 | A1 * | 3/2006 | Woodward ......... | A61K 31/4745 424/85.1 |
| 2009/0182004 | A1 * | 7/2009 | Winckle ............... | A61K 9/0014 514/293 |
| 2011/0293658 | A1 | 12/2011 | Cerundolo et al. | |

FOREIGN PATENT DOCUMENTS

| | | |
|---|---|---|
| JP | 2010-520851 A | 6/2010 |
| KR | 10-2006-0096415 A | 9/2006 |
| KR | 10-2010-0137449 A | 12/2010 |

OTHER PUBLICATIONS

InvivoGen—http://www.invivogen.com/tlr7-8-base-analog, 2018 (Year: 2018).*
American Liver Foundation, (https://liverfoundation.org/for-patients/about-the-liver/diseases-of-the-liver/, 2017) (Year: 2017).*

(Continued)

*Primary Examiner* — Umamaheswari Ramachandran
(74) *Attorney, Agent, or Firm* — Vorys, Sater, Seymour & Pease LLP; Mih Suhn Koh

(57) ABSTRACT

The present invention is based on the fact that imiquimod, which is a substance that enhances Toll-like receptor 7 (TLR7) related to the innate immunity of a living body, is effective in the prevention and treatment of obesity or liver disease, and the present invention relates to a pharmaceutical composition for the prevention and treatment of obesity or liver disease, wherein the TLR7 agonist used for the immune system disease inhibits fatty acid synthetase (FAS), activates autophagosome or inhibits IGF-1.

2 Claims, 5 Drawing Sheets

(56) References Cited

OTHER PUBLICATIONS

Funk et al. (J of Translational Medicine, 2014, p. 1-8) (Year: 2014).*
Horsmans et al. (Hepatology, 42, 3, 2005, p. 724-731). (Year: 2005).*
Milic et al. (World J of Gastroenterology, 2014, 12, 20(28), 9330-9337). (Year: 2014).*
Vozzo, 2018, Cleveland Clinic, http://www.clevelandclinicmeded.com/medicalpubs/ diseasemanagement/hepatology/alcoholic-liver-disease/ (Year: 2018).*
Alisi et al., "Pathogen- or Damage-Associated Molecular Patterns During Nonalcoholic Fatty Liver Disease Development", Hepatology, vol. 54, No. 5, pp. 1500-1502, (2011).

* cited by examiner

PHARMACEUTICAL COMPOSITION FOR PREVENTING AND TREATING OBESITY OR LIVER DISEASES, CONTAING TLR7 AGONIST

BACKGROUND

Technical Field

The present invention is based on the fact that imiquimod, which is a substance that enhances Toll-like receptor 7 (TLR7) related to the innate immunity of a living body, is effective in the prevention and treatment of obesity or liver disease, and relates to a pharmaceutical composition for the prevention and treatment of obesity or liver diseases including TLR7 agonists used in immune system diseases.

Background Art

Over-accumulation of body fat is known to be a major cause of obesity, diabetes, hyperlipidemia, fatty liver, cardiovascular disease and cancer. Among these, fatty liver is a disease in which Neutral fat accumulates in hepatocytes and can be divided into nonalcoholic and alcoholic fatty liver, and fatty liver due to fat accumulation due to obesity is classified as nonalcoholic.

In addition, fatty liver induced by excessive alcohol intake, or nonalcoholic fatty liver induced by high fat and low immunity is one of the causes of various liver diseases. In general, fatty accumulation in hepatocytes leads to fatty liver, resulting in liver cirrhosis leading to hepatic cirrhosis and liver cancer. Therefore, an effective early treatment for obesity or fatty liver, which is considered to be an early disease of liver disease, is very necessary.

However, until now, there has been no effective drug treatment for nonalcoholic fatty liver disease, and it depends on basic prescription such as weight loss through dieting, exercise, etc., so that it is necessary to develop new therapeutic agents by clarification of cellular signaling system for obesity or fatty liver.

Meanwhile, TLR7 (toll-like receptor) is one of the factors constituting the detection system of innate immune. TLR7 proteins are buried in cellular membranes and respond only to specific stimuli. Once TLR7 acquires activity through a specific stimulus, the pathway to activate the defense mechanism of the immune system begins to work in earnest.

Imiquimod is a TLR7 agonist and ligand, and a biochemical agent that induces active stimulation of TLR7. As an immunosuppressant approved by the US FDA on Feb. 27, 1997, it is used as an antiviral agent and is mainly used for external skin application.

US Patent Publication No. US 20100130425 A1 discloses that a pharmaceutical composition containing a TLR7 agonist such as imiquimod is effective for diseases such as anemia and hypoxia, etc., and Korean Laid-Open Publication No. 10-2013-0016130 discloses that Imiquimod, which is a stimulant of TLR7, treats carcinomas such as colorectal cancer, liver cancer and melanoma as well as immunological activity, and has been shown that it can be used as an adjuvant for anticancer therapy by discovering that it induces autophagocytosis through activation of active oxygen species and promotes apoptosis.

In addition, Korean Laid-Open Publication No. 10-2013-004315 discloses that inhibitors of TLR7 and/or TLR9 are effective for autoimmune diseases, and Korean Laid-Open Publication No. 10-2006-0096415 discloses that TLR7 ligand is effective for infection by hepatitis C virus.

However, it is not known that TLR7 agonists are effective in liver disease, but in the international journal Hepatology, TLR7 is associated with hepatic fibrosis, suggesting that it can be approached as a therapeutic agent.

Therefore, the present invention has been accomplished by discovering the possibility of TLR7 agonist inducing the therapeutic effect of fatty liver among liver diseases having a high prevalence rate globally.

The prior art is as follows.
US20100130425 A1
KR1020130016130 A
KR102013004315 A
KR1020060096415 A
Hepatology, 2014, Vol. 60(1), pp. 237-49

DETAILED DESCRIPTION OF THE INVENTION

Summary

The present invention discloses that TLR7 agonist, immune system disease treatment, is effective for the prevention and treatment of obesity or liver disease, and based on the facts, the present invention provides a pharmaceutical composition for prevention and treatment of obesity or liver disease comprising TLR7 agonist as an active ingredient, a functional food containing the same, and a therapeutic aid supplement.

Technical Solution

The present invention provides a pharmaceutical composition for prevention and treatment obesity or liver disease comprising a TLR7 agonist as an active ingredient and a pharmaceutically acceptable carrier.

TLR7 agonist is an imiquimod represented by the following Formula (1).

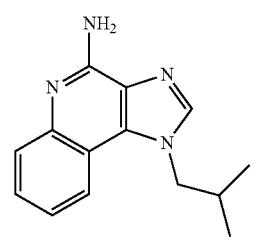

Formula (1)

Further, the liver disease is any one of fatty liver, hepatitis, and liver cirrhosis, and the fatty liver is effective for nonalcoholic fatty liver or alcoholic fatty liver, and most preferably for nonalcoholic fatty liver.

The hepatitis is also effective for an A type acute hepatitis, a B type acute hepatitis, a B type chronic hepatitis, a C type acute hepatitis and a C type chronic hepatitis.

In addition, the TLR7 agonist according to the present invention is characterized by inhibition of fatty acid synthase (FAS), activation of autophagosome, or inhibition of IGF-1.

As another specific example of the present invention, there is provided a functional food composition comprising imiquimod as an active ingredient for preventing and improving obesity or liver disease.

The food composition may be provided in the form of a gum, a tablet, a biscuit, a beverage, etc., and may be provided as a vitamin complex, a health supplement, a food for special effect supplement, or the like.

The pharmaceutical composition for prevention and treatment of liver disease according to the present invention can be used in the form of a general pharmaceutical preparation and can be used as a health functional food for the purpose of prevention and improvement of liver disease.

The TLR7 agonists of Formulas 1 to 3 according to the present invention can be formulated into pharmaceutical preparations for oral administration by mixing pharmaceutically acceptable excipients, binders, disintegrants, lubricants, surfactants, cosolvents, sweeteners and the like. As the excipient, microcrystalline cellulose, lactose, corn starch, mannitol, low-substituted hydroxypropylcellulose, magnesium metasilicate aluminate, colloidal silicon dioxide and the like are preferable, and as the binder, hydroxypropylmethylcellulose, povidone, hydroxypropylcellulose and the like are preferable, and as the disintegrant, sodium croscarmellose, sodium starch glycolate, calcium carboxymethylcellulose, crospovidone and the like are preferable, and as the lubricant, magnesium stearate, talc, sodium stearyl fumarate and the like are preferable.

Surfactants include pharmacologically acceptable polyoxyethylene sorbitan fatty acid esters, polyoxyethylene polyoxypropylene block copolymer, macrogol glycerol hydroxystearate, and sodium lauryl sulfonate, which may be used alone or in combination of two or more complex. The cosolvent include a single or complex composition such as propylene carbonate, propylene glycol, ethanol, transcutol (diethylene glycol monoethyl ether), glycofurol (tetrahydrofurfuryl alcohol polyethylene glycol ether), and polyethylene glycol and the like. Of these, propylene carbonate, propylene glycol, and polyethylene glycols may be preferably used alone or in combination of 2 or more.

The present invention can be used for the preparation of pills, powders, granules, tablets, capsules, liquid preparations and the like as a preparation for oral administration, and in addition to the above-described effective ingredients, the present invention further comprises one or more pharmaceutically acceptable carriers for administration, and the pharmaceutically acceptable carrier may be a mixture of saline, sterilized water, Ringer's solution, buffered saline, dextrose solution, maltodextrin solution, glycerol, ethanol and one or more of these components, and if necessary, other conventional additives such as an antioxidant, a buffer, and a bacteriostatic agent may be added. In addition, diluents, dispersants, surfactants, binders, and lubricants may be added to form injectable formulations such as aqueous solutions, suspensions, emulsions, and the like.

Formulations for parenteral administration include sterile aqueous solutions, non-aqueous solutions, suspensions, emulsions, freeze-dried preparations, and suppositories. Examples of the non-aqueous solvent and suspending agent include propylene glycol, polyethylene glycol, vegetable oil such as olive oil, injectable ester such as ethyl oleate, and the like. As a suppository base, witepsol, macrogol, tween 61, cacao paper, laurin, glycerogelatin and the like can be used. In addition, the pharmaceutical composition of the present invention can be mixed with distilled water for injection to have a saline concentration similar to body fluids, and can be prepared with a Ringer's solution.

In addition, the dose of the TLR7 agonist compound according to the present invention varies depending on the patient's body weight, age, sex, health condition, diet, administration time, administration method, excretion rate and severity of disease, and it is preferable to take the dose of 0.01 mg/kg to 1000 mg/kg on an adult basis once or several times a day.

The pharmaceutical composition for prevention and treatment of obesity or liver disease comprising the TLR7 agonist of the present invention can be administered to mammals such as rats, livestock, and humans in various routes. All modes of administration may be expected and may be administered, for example, by oral, rectal, or intravenous, intramuscular, subcutaneous, intra-dermal, or intracerebral injection.

The present invention provides a health functional food comprising a TLR7 agonist and a pharmaceutically acceptable food supplementary additive exhibiting a preventive effect of obesity or liver disease. Examples of health functional foods to which TLR7 agonists can be added include various general foods, beverages, gums, tea, and vitamin complexes. In addition, the TLR7 agonist may be added to food or beverage for the purpose of preventing obesity or liver disease.

The amount of the TLR7 agonist in the food or beverage may be 0.01 to 15% by weight of the total food weight, and the health drink composition may be added at a ratio of 0.02 to 5 g, preferably 0.3 to 1 g, based on 100 g.

In addition, the present invention can be manufactured by pouches, beverages, or other liquids when prepared as a liquid formulation, and can be manufactured by using as a main or supplementary ingredient of the food or by adding to other foods. Food-acceptable food additives may be used at this time.

The health functional beverage composition of the present invention is not particularly limited to the other ingredients, as long as it contains the above-mentioned active ingredient as an essential ingredient in the indicated ratio, and may contain additional ingredients such as various flavors or natural carbohydrates such as ordinary beverages. Examples of the above-mentioned natural carbohydrates include monosaccharides; disaccharides; and polysaccharides, and these are glucose, fructose, maltose, sucrose, and conventional sugars such as dextrin, cyclodextrin and the like, and sugar alcohols such as xylitol, sorbitol, erythritol and the like. Other than the above, flavors include natural flavors and synthetic flavors, and natural flavors include tau martin, stevia extract, rebaudioside A, glycyrrhizin, etc. and synthetic flavors include saccharin, aspartame and the like. The ratio of the natural carbohydrate is generally about 1 to 20 g, preferably about 5 to 12 g per 100 g of the composition of the present invention. In addition to the above, the active ingredient of the present invention may contain various nutrients, vitamins, minerals (electrolytes), synthetic and natural flavors, coloring agents and thickening agents (cheese, chocolate etc.), pectic acid and its salts, alginic acid and its salts, protective colloid thickener, pH adjusting agents, stabilizers, preservatives, glycerin, alcohols, carbonating agents used in carbonated drinks, and the like. In addition, the active ingredient of the present invention may contain flesh for the production of natural fruit juice, fruit juice drink and vegetable drink. These components may be used independently or in combination. At this time, although the ratio of the additive is not critical, it is generally selected from the range of 0.01 to about 20 parts by weight per 100 parts by weight of the active ingredient of the present invention.

Effects of the Invention

The present invention relates to a pharmaceutical composition for the prevention and treatment of liver disease comprising an TLR7 agonist such as imiquimod as an active ingredient. TLR7 agonists inhibit hepatic cell fat accumulation, and since it is highly effective in inhibiting hepatomegaly and fat accumulation in a liver-derived mouse fed with high-fat diets, it can be easily used as a therapeutic agent for fatty liver or obesity.

DETAILED DESCRIPTION

Hereinafter, preferred embodiments of the present invention will be described in detail. In the following description, numerous specific details are set forth, such as specific elements, and it will be understood by those of ordinary skill in the art that various changes in form and detail may be made therein without departing from the spirit and scope of the present invention as defined by the following claims. Further, in the following description of the present invention, when related announcements or a detailed description of the configuration may unnecessarily obscure the gist of the present invention, a detailed description thereof will be omitted.

Example 1

Imiquimod, a TLR7 agonist for cell treatment and intraperitoneal injection, was purchased from invivogen. The formula of the purchased preparation is shown in Formula (1). In order to adjust the concentration, physiological saline was used for dilution.

<Example 2> Estimation of Fat Accumulation in Fatty Liver Cell Model of Imiquimod Mouse Liver Cells Before Fat Induction
The imiquimod purchased in Example 1 was tested in cells. Mouse hepatocytes were obtained by cellizing liver tissues isolated from normal C57BL6/J mice and TLR7 KO mice lacking the TLR7 gene and fat accumulation was induced by treatment with 10 mM of unsaturated fatty acid (UFAs) mixed with arachidonic acid (Sigma, USA) and oleic acid (Sigma, USA) 1:1.

Cells were incubated at 37° C., 5% of $CO_2$. DMEM (Dulbecco's modified Eagle's medium) containing 10% fetal bovine serum (FBS) and antibiotic (penicillin/streptomycin; Gibco, USA) was used as the cell culture medium. Every two days, the surface of the cultured cells was washed with phosphate buffered saline (PBS) and cells were isolated by treatment with 0.5% trypsin and then subcultured.

The imiquimod was treated at the concentration of 10 μg/ml 1 hour before the start of the experiment. UFAs were then added and the fat accumulation was assessed after 48 hours.

Figure 1:
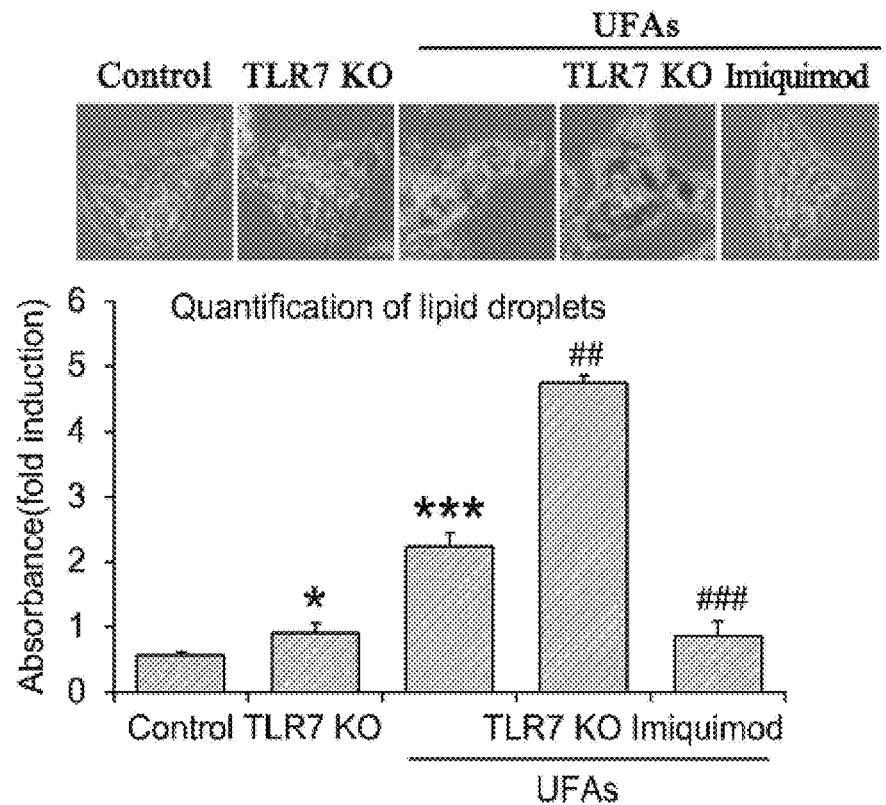
FIG. 1 relates to the inhibition of fat accumulation of imiquimod in the treatment of UFAs inducing fat accumulation in mouse hepatocytes.

Oil-Red-o Reagent Dyeing
In order to confirm that imiquimod inhibits the fat accumulation effect in hepatocytes, the cells were cultured for 48 hours after the reagent treatment according to the method of Example 2 above. The cells were stained with an oil-red-o reagent (Lifeline Cell Technology, Carlsbad, Calif., USA) and the accumulation of fat was visually evaluated (FIG. 1).

Fat Content Measurement
When the group was treated with isopropanol to destroy the cell membrane and the absorbance at 540 nm was measured, as in the visual evaluation, it was confirmed that the level of fat in the group treated with imiquimod was lower than that in the group without treatment.

Transcription Factor of Lipid Differentiation Induction
To determine the level of RNA expression at the gene level of fatty acid synthase (FAS), SREBP-1 (sterol regulatory element binding protein-1), PPARγ (peroxisome proliferator-activated receptor), and aP2 (fatty acid binding protein 4), real time RT-PCR (ABI Step One Plus Sequence System, Applied Biosystems, Singapore) was performed. The PPARγ and FAS are directly related to fat metabolism, and since the metabolism is regulated by the aP2 and SREBP-1 factor, it was determined whether imiquimod affects the factor.

Figure 2:
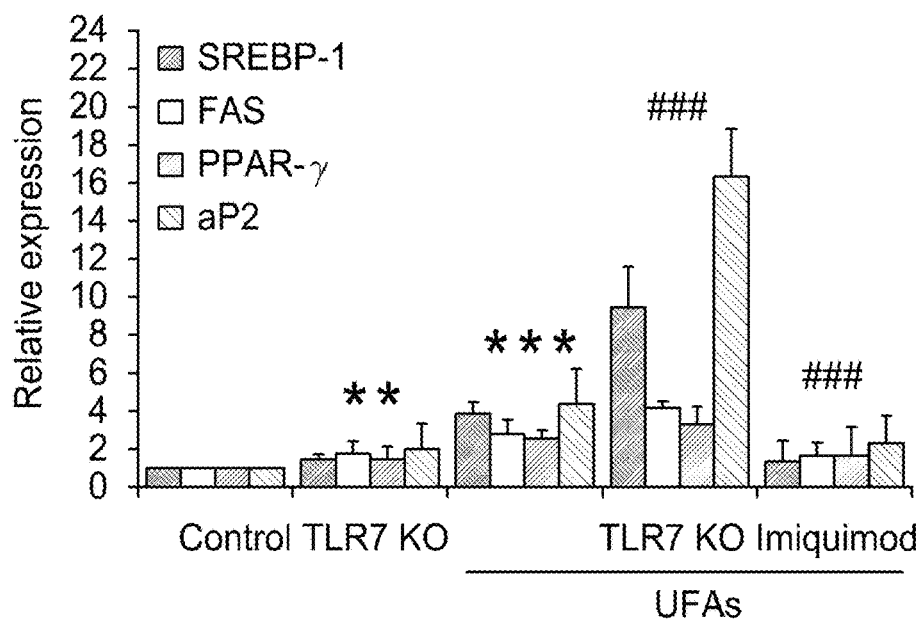
FIG. 2 shows the results of real time RT-PCR of the mRNA isolated from hepatocytes to compare the expression level of the fat-derived gene.

As shown in FIG. 2, the degree of expression of SREBP-1, FAS, aP2 and PPARγ were measured, and imiquimod inhibited the expression of the factor. From the above results, it was confirmed that imiquimod inhibited lipid accumulation in hepatocytes through inhibition of SREBP-1, FAS, aP2 and PPARγ gene expression.

Figure 3:
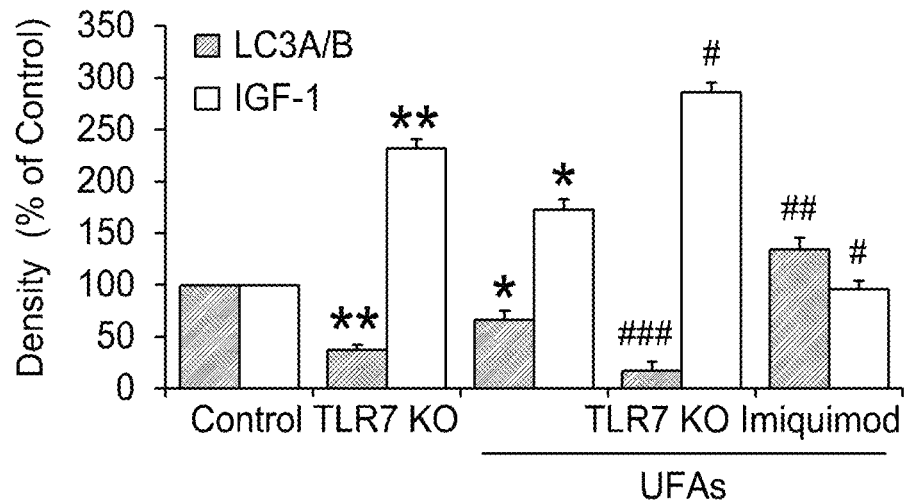
FIG. 3 shows the results of analysis of the levels of LC3A/B, an indicator of autophagosome, and IGF-1, a hepatocyte-producing protein, using immunoblot analysis for proteins isolated from hepatocytes.

Comparison and Evaluation of Autophagosome and IGF-1
In FIG. 3, expression of autophagosome associated with congenital immunity and IGF-1 associated with fatty liver development was compared and evaluated. According to recently published international journals, It has been reported that as the expression of LC3A/B, an indicator of autophagosome increases, fatty liver improves, and as IGF-1 is inhibited, the fatty liver improves. Correspondingly, in the above results, when LC3A/B inhibited by UFAs and increased IGF-1 are treated with imiquimod, significant increases and decreases were confirmed by immunohistochemistry in proteins isolated from hepatocytes.

<Example 3> Inhibitory Effect of Imiquimod on Fatty Liver In Vivo

C57BL6/J mice (Daehan Biolink, Daejeon, Korea) that induced obesity with feed containing 45% UFAs for 8 weeks and a knockout mouse (TLR7 KO) from Dr. Akira (Osaka University, Suita, Japan) in which TLR7 is not inherently present, were used. For this purpose, imiquimod was injected twice a week at a concentration of 0.1 mg/kg, while fatty liver model was made by feeding only high unsaturated fat diet (UFAs diet with 45% of the calories, Daehan Biolink, Daejeon, Korea) for 8 weeks.

Figure 4:
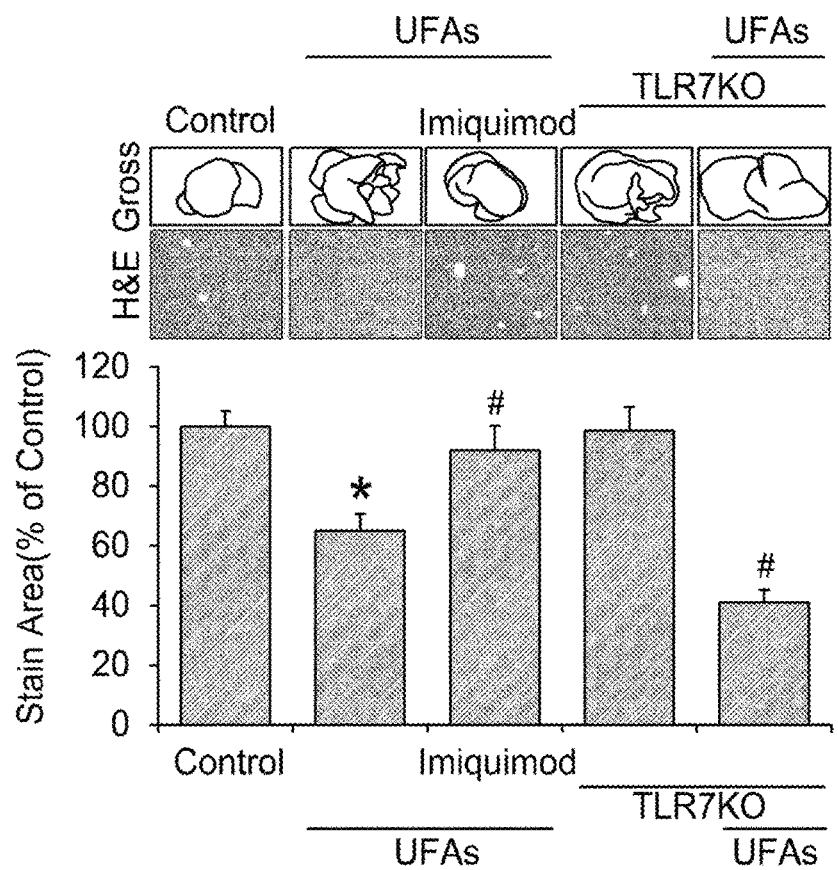
FIG. 4 relates to the effect of imiquimod on the fatty liver induced in mice.

From the above results, evaluation of liver tissue after 8 weeks showed significant inhibition of the development of fatty liver in the group injected with imiquimod (FIG. 4). As a result of H & E staining of tissue sections, balloon, a sign of fat accumulation between cells and cells, was found in UFAs fed mice, which was confirmed to be improved by imiquimod injection. In addition, when UFAs were injected in TLR7 KO mice, more severe balloon was formed, therefore TLR7 was found to be very important in the production of fatty liver. From this, it was confirmed that imiquimod, a TLR7 agonist effectively inhibited fatty liver.

Figure 5:
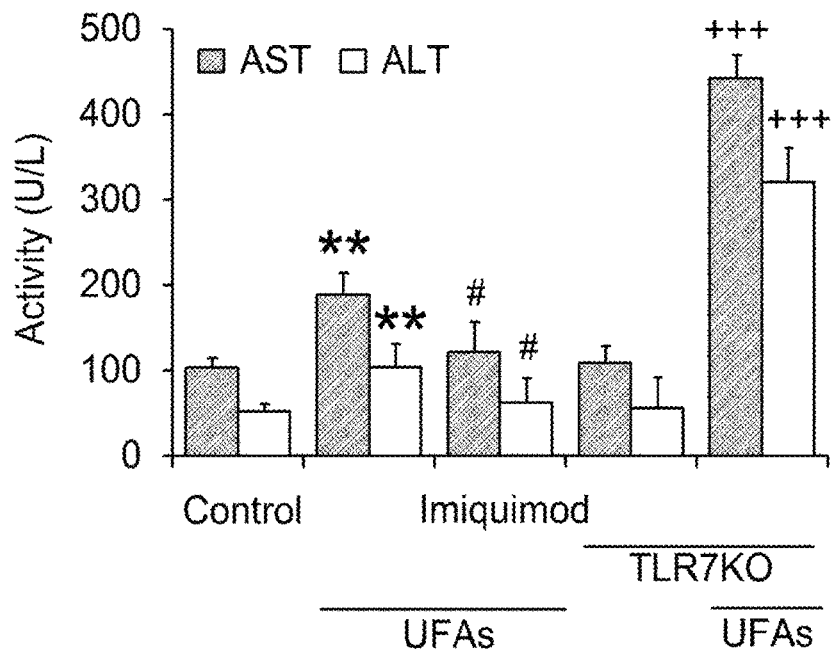
FIG. 5 is a graph showing the liver water level contained in the serum of a mouse.
Figure 6:
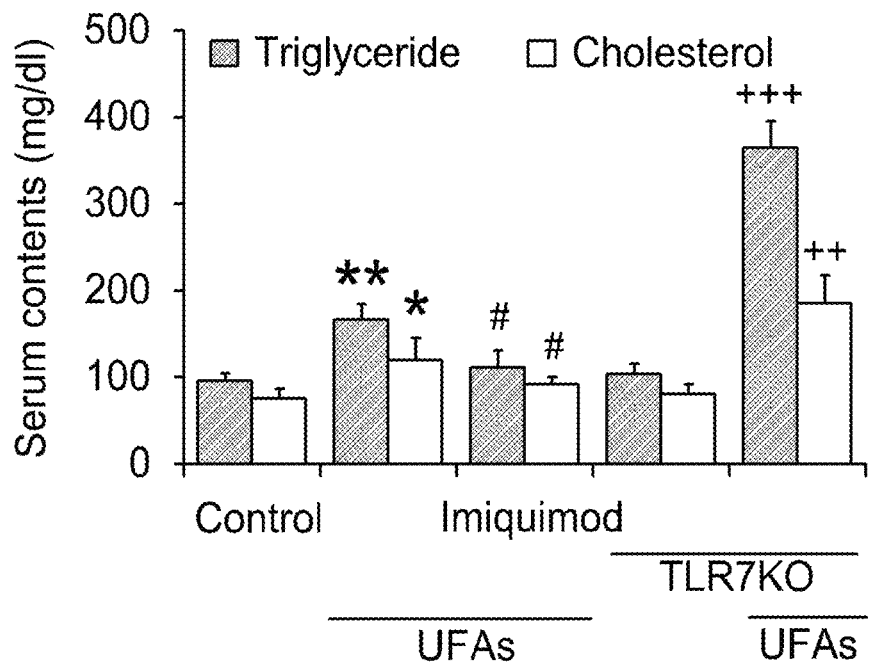
FIG. 6 shows the levels of triglyceride and cholesterol contained in the serum of mice.

<Example 4> Serological Analysis and Histological Analysis of Inhibitory Effect of Imiquimod on Fatty Liver Serological Analysis Through analysis of the serum isolated from the mouse group, aspartate aminotransferase (AST) and alanine aminotransferase (ALT), which are indicators of liver status, were evaluated as shown in FIG. 5, and the triglyceride content and total cholesterol content (FIG. 6) were analyzed using a biochemical serum analyzer, VetTest 8008 (IDEXX, Korea).

As can be seen from the results of FIG. 5, the levels of AST and ALT in mice serum with fatty liver progression due to UFAs feed were increased, but the levels of imiquimod-treated mice were significantly decreased. For TLR7 KO mice, it was confirmed that the levels of AST and ALT due to UFAs feed supplement were excessively increased. Triglycerides and cholesterol also showed similar trends. For mice fed UFAs feed, the triglyceride and cholesterol levels were significantly increased, and this was significantly reduced by imiquimod administration. For TLR7 KO mice, it was found that the levels of triglyceride and cholesterol were excessively increased when the UFAs feed was fed.

Histological Analysis

Figure 7:
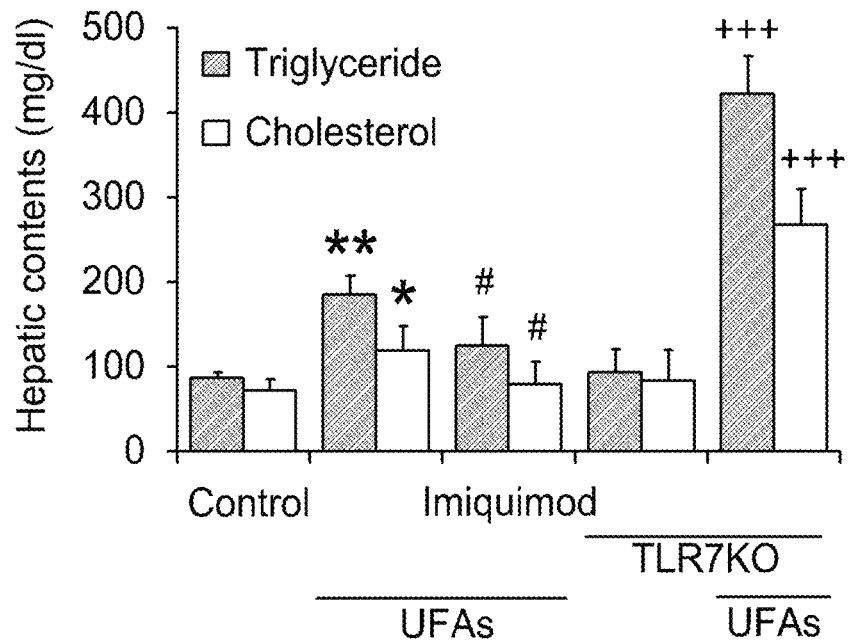
FIG. 7 is a graph showing the levels of triglyceride and cholesterol contained in liver tissues of mice.

The liver tissues separated from the mouse were finely crushed to prepare analytical samples, and the levels of triglyceride and cholesterol were measured using Enzyme Linked ImmunoSorbent Assay (ELISA) (FIG. 7). The above results were confirmed similarly to the results of serum analysis, and significant reductions in the levels of triglyceride and cholesterol in liver tissue were observed with imiquimod administration. In liver tissue of TLR7 KO mice, when UFAs were fed to induce fatty liver, it showed overwhelming accumulation of triglyceride and cholesterol.

Figure 8:
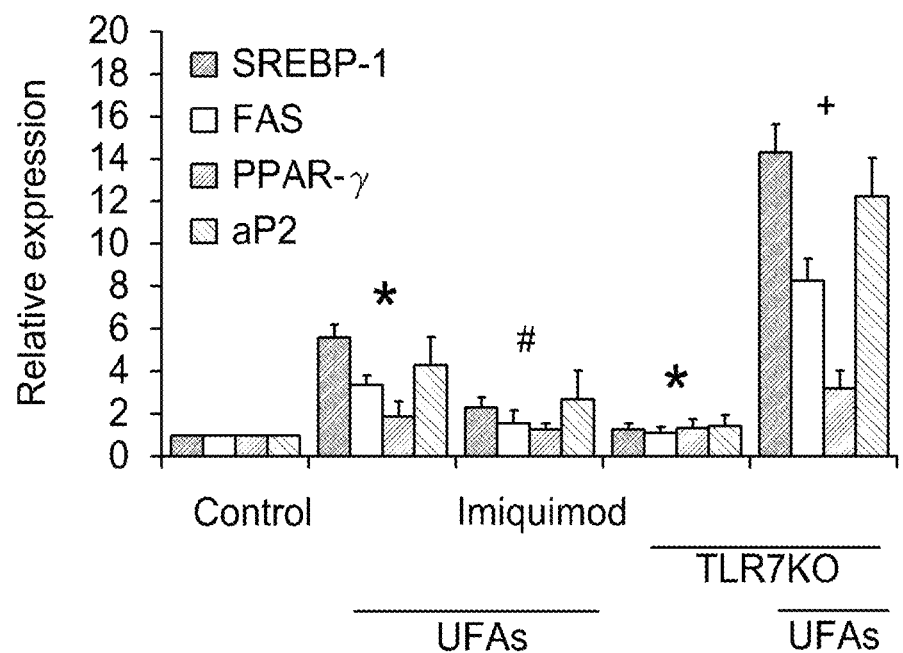
FIG. 8 shows the results of real time RT-PCR of mRNA isolated from mouse liver tissues to compare the expression levels of fat-derived genes.
Figure 9:
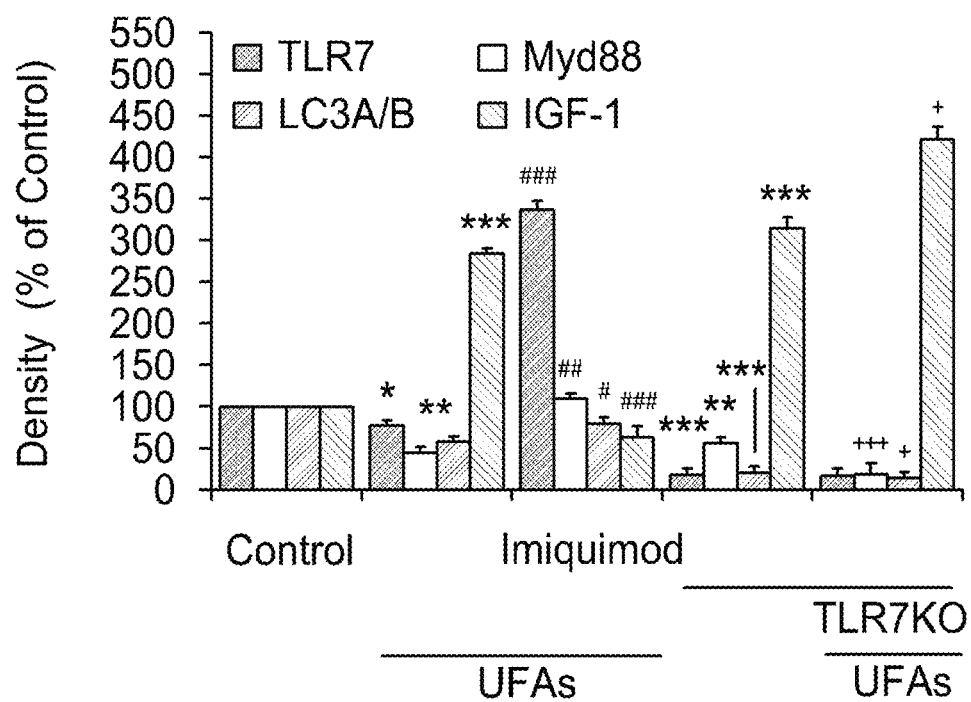
FIG. 9 shows the results of analysis of TLR7, its transcription factor, Myd88, and LC3A/B, an indicator of autophagosome, and IGF-1, a hepatocyte production protein, using immunohistochemistry.

Real-time RT-PCR analysis using mRNA isolated from liver tissue confirmed the degree of amplification of fat-derived genes, and this showed similar trends to the results of cell experiments (FIG. 8). Fat-induced genes such as SREBP-1, FAS, PPAR-γ, and aP2 were increased in liver tissues from liver-derived mice fed UFAs compared to the control group. This was significantly reduced in the liver tissue of mice treated with imiquimod. Feeding UFAs to TLR7 KO mice showed a significant increase in fat-induced genes.

Autophagosome associated with congenital immunity, and expression of IGF-1 associated with fatty liver development were compared and evaluated with proteins isolated from liver tissue. Similar to the protein isolated from the hepatocytes, and expression of TLR7 and its downstream transcript Myd88 was also confirmed, and as a result, we confirmed that imiquimod affects the expression of LC3A/B, an autophagosome marker, and IGF-1, a hepatocyte-producing protein, through TLR7 hyperactivity. It was confirmed that LC3A/B inhibited by fatty liver induced by UFAs, and increased IGF-1 expression were significantly increased and decreased upon administration of imiquimod by immunohistochemistry in proteins isolated from hepatocytes.

As a result, the present invention confirms that imiquimod has a biological activity capable of reducing and alleviating the degree of fatty liver induced by highly unsaturated fat mix from the cell experiments and in vivo animal experimental results.

What is claimed is:

1. A method of inhibiting liver fat accumulation in mammals in need thereof, comprising administering by intraperitoneal injection to the mammals an effective amount of imiquimod having the following structure as a TLR7 agonist to inhibit liver fat accumulation:

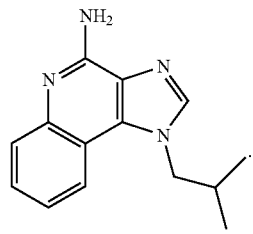 [SMILES: CC(C)Cn1cnc2c(N)nc3ccccc3c21]

2. The method of claim 1, wherein imiquimod inhibits liver lipid accumulation through inhibition of SREBP-1, FAS, aP2 and PPARγ gene expression, activates autophagosome, or inhibits IGF-1.

* * * * *